United States Patent
Marek et al.

(10) Patent No.: US 11,553,931 B2
(45) Date of Patent: Jan. 17, 2023

(54) TEMPERATURE SENSOR FOR A BONE DRILL

(71) Applicant: OsteoMed LLC, Addison, TX (US)

(72) Inventors: Matthew Geoffrey Marek, Plano, TX (US); Crystal Johnson, Garland, TX (US); Laith Radaydeh, Garland, TX (US); Julian De Las Salas, Cypress, TX (US); Francisco Enriquez-Garces, Irving, TX (US); Caleb Cyrill, Austin, TX (US); Jose Montemayor-Rodriguez, Flower Mound, TX (US)

(73) Assignee: OsteoMed LLC, Addison, TX (US)

( * ) Notice: Subject to any disclaimer, the term of this patent is extended or adjusted under 35 U.S.C. 154(b) by 286 days.

(21) Appl. No.: 17/073,105

(22) Filed: Oct. 16, 2020

(65) Prior Publication Data

US 2021/0113218 A1    Apr. 22, 2021

Related U.S. Application Data

(60) Provisional application No. 62/916,115, filed on Oct. 16, 2019.

(51) Int. Cl.
*A61B 17/16* (2006.01)
*A61B 17/00* (2006.01)

(52) U.S. Cl.
CPC ...... *A61B 17/1626* (2013.01); *A61B 17/1617* (2013.01); *A61B 2017/00084* (2013.01); *A61B 2017/00128* (2013.01); *A61B 2560/0266* (2013.01); *A61B 2560/0443* (2013.01); *A61B 2560/0462* (2013.01); *A61B 2562/0271* (2013.01)

(58) Field of Classification Search
CPC . A61B 17/16; A61B 17/1613; A61B 17/1615; A61B 17/1617; A61B 17/162; A61B 17/1622; A61B 17/1624; A61B 17/1626; A61B 17/1628; A61B 2017/00084; A61B 2560/0266; A61B 2560/0462; A61B 2562/0271
See application file for complete search history.

(56) References Cited

U.S. PATENT DOCUMENTS

| | | | |
|---|---|---|---|
| 10,398,517 B2 * | 9/2019 | Eckert | A61B 18/085 |
| 11,376,082 B2 * | 7/2022 | Shelton, IV | A61B 90/98 |
| 2016/0361070 A1 * | 12/2016 | Ardel | A61B 17/1617 |
| 2018/0049792 A1 * | 2/2018 | Eckert | A61B 34/30 |
| 2020/0405405 A1 * | 12/2020 | Shelton, IV | G16H 40/67 |
| 2021/0113218 A1 * | 4/2021 | Marek | A61B 17/1626 |
| 2021/0298852 A1 * | 9/2021 | Crosetti | A61B 1/2676 |

FOREIGN PATENT DOCUMENTS

| | | | | |
|---|---|---|---|---|
| CN | 107847236 A | * | 3/2018 | ......... A61B 17/1617 |
| CN | 107921554 A | * | 4/2018 | ......... A61B 17/1617 |
| CN | 114072090 A | * | 2/2022 | ........... A61B 17/072 |
| WO | WO-2016199153 A1 | * | 12/2016 | ......... A61B 17/1617 |
| WO | WO-2020260999 A1 | * | 12/2020 | ........... A61B 17/072 |

* cited by examiner

*Primary Examiner* — Eric S Gibson
(74) *Attorney, Agent, or Firm* — K&L Gates LLP

(57) ABSTRACT

In a particular implementation, an apparatus configured to measure bone temperature during drilling includes a processor and an infrared (IR) sensor coupled to the processor and configured to measure temperature data indicating a temperature at an interface between a drill bit and a bone of a patient.

22 Claims, 7 Drawing Sheets

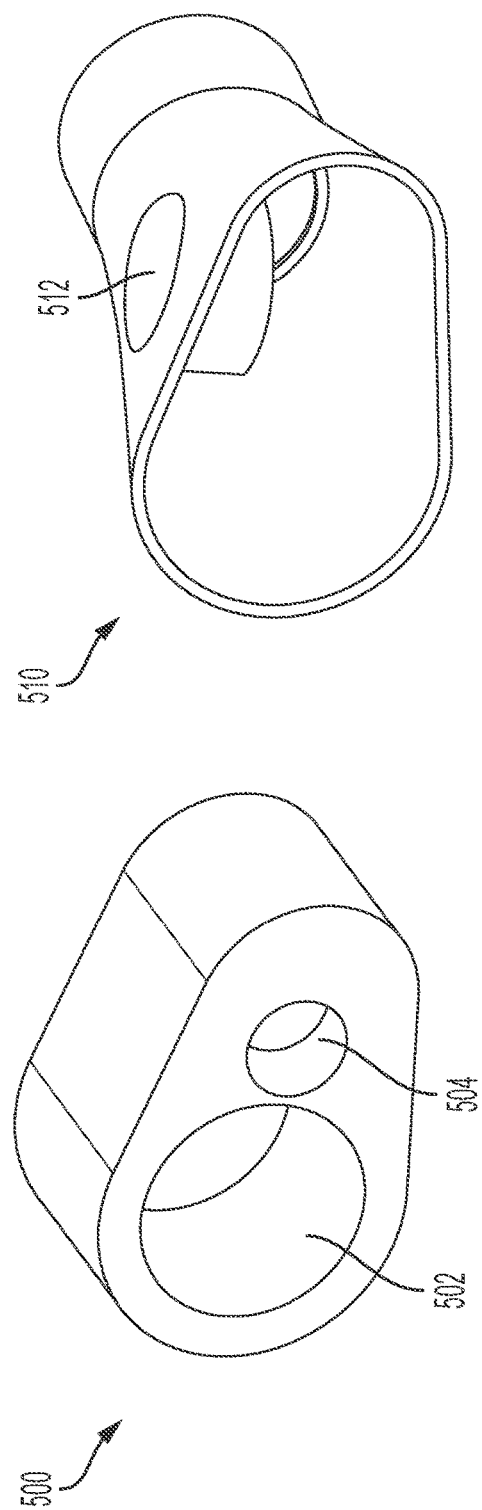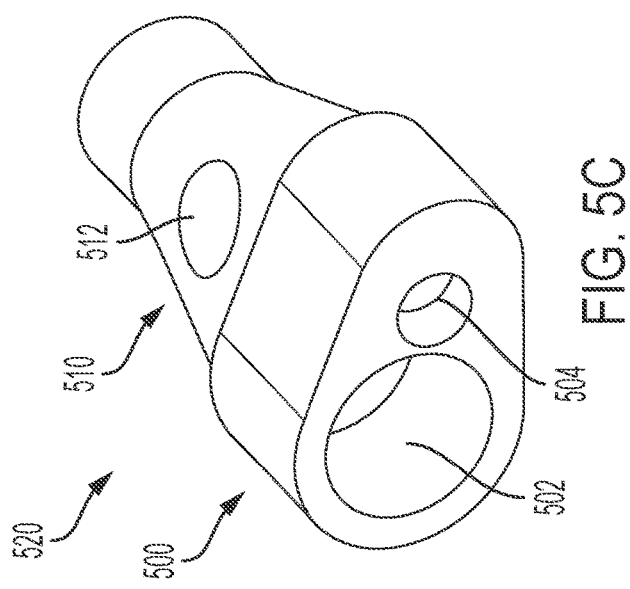

TEMPERATURE SENSOR FOR A BONE DRILL

CROSS-REFERENCE TO RELATED APPLICATIONS

The present application claims priority to U.S. Provisional Application No. 62/916,115 filed Oct. 16, 2019 and entitled "TEMPERATURE SENSOR FOR A BONE DRILL," the disclosure of which is incorporated by reference herein in its entirety.

TECHNICAL FIELD

The present disclosure generally relates to bone drills, and more particularly, to a temperature sensor for a bone drill.

BACKGROUND

Drilling into a patient's bone is a common task for a surgeon to perform. For example, surgeons may drill into a patient's bone when inserting a component, such as a screw, as part of a therapeutic surgery. However, there are multiple considerations that a surgeon must take into account. One such consideration occurs when the grinding of a bone with a drill bit creates heat at the interface between the drill bit and the bone. If sufficient heat is generated (e.g., 47° Celsius or higher), bone cells may be killed by the excessive heat, which can weaken the bone, kill nearby cells, cause nerve damage, and/or cause an inserted screw not to fixate properly. To prevent excess temperature buildup, surgeons currently use a combination of manual technique, experience, and irrigation. However, even a small misjudgment by the surgeon can result in damage to the bone cells due to excess heat, which can cause permanent damage to the patient and/or can increase recovery time.

SUMMARY

The present disclosure describes apparatuses, methods, and systems for measuring (and therefore preventing) excess heat during a bone drilling process, thereby preventing unintentional death/damage of bone cells. To illustrate, an apparatus may include a temperature sensor, such as an infrared (IR) sensor, that is configured to measure the temperature at an interface between a drill bit and a bone of a patient. The apparatus may also provide an indication (e.g., feedback information) to the surgeon of the measured temperature. As an example, the apparatus may include a light emitting diode (LED) that emits different colored light based on the temperature. For example, the LED may emit green light when the temperature is within a first temperature range (e.g., a "safe" range), the LED may emit yellow light when the temperature is within a second range (e.g., a "border" range), and the LED may emit red light when the temperature is within a third range (e.g., a "dangerous" range). Additional features may be added to these LED indications such as flashing before switching to the next level, and such flashing may include increases/decreases in periodicity as temperature increases or decreases.

Additionally, or alternatively, the apparatus may include a speaker that outputs an audio output when the temperature satisfies a threshold (e.g., when the temperature reaches the dangerous range, or when the temperature is within the dangerous range for a threshold amount of time, such as 20 seconds). In some implementations, the apparatus may also include a display device that displays the temperature to the surgeon. In this manner, the surgeon may be aware of the temperature of the bone during the drilling process, and can slow down or pause the process if the temperature becomes high enough that there is a risk of killing bone cells.

In some implementations, the apparatus may be an attachment that is configured to be coupled to a drill. For example, the attachment may include a rigid body and a casing that houses the IR sensor, the LED, and a laser that indicates a location to which the IR sensor is directed. The attachment may be able to be snapped onto a drill and removed after the process is over, such that the attachment may be sanitized and re-used during another process or with a different drill. The attachment may be sufficiently sized such that the attachment does not significantly affect the size of the drill or the surgeon's comfort using the drill. In other implementations, the components of the apparatus described herein may be integrated into the drill. For example, a drill may include an IR sensor that is directed to the end of the drill bit (e.g., to an interface between the drill bit and the bone), as well as an LED, as speaker, or a combination thereof.

In a particular aspect, an apparatus configured to measure bone temperature during drilling includes a processor and an infrared (IR) sensor communicatively coupled to the processor and configured to measure temperature data indicating a temperature at an interface between a drill bit and a bone of a patient.

The apparatus may further include a laser configured to emit a light at a location where the IR sensor is directed. Additionally, or alternatively, the apparatus further includes one or more light emitting diodes (LEDs) configured to emit one of a plurality of colored lights based on the temperature indicated by the temperature data. In some such implementations, an LED is configured to: emit a first colored light based on the temperature being within a first temperature range, emit a second colored light based on the temperature being within a second temperature range, and emit a third colored light based on the temperature being within a third temperature range.

In some aspects, the apparatus further includes a speaker configured to emit an audio output based on the temperature indicated by the temperature data satisfying a threshold. Additionally, or alternatively, the apparatus further includes a display device configured to display the temperature indicated by the temperature data. In some such aspects, the display device is configured to display the temperature indicated by the temperature data.

In some aspects, the apparatus further includes a rigid body coupled to the IR sensor. In some such implementations, the rigid body includes an attachment to a drill. In some such aspects, the apparatus further includes one or more attachment clips configured to couple the attachment to the drill. Alternatively, the IR sensor may be integrated within a drill.

In another particular aspect, a method of measuring bone temperature during drilling includes detecting a temperature at an interface between a drill bit and a bone of a patient using an infrared (IR) sensor. The method also includes outputting an indication based on the temperature.

The indication may be a visual indication, and the visual indication is output by a light emitting diode. Additionally, or alternatively, the indication is an audio indication, and the audio indication is output by a speaker. Additionally, or alternatively, the method further includes visually displaying the temperature at a display device. Additionally, or alternatively, the method further includes adjusting a power level provided to a drill based on the temperature. In another particular aspect, a system includes a drill configured to drill into bone of a patient. The drill includes a drill bit. The system further includes a temperature monitoring system. The temperature monitoring system includes an infrared (IR) sensor configured to measure a temperature at an interface of the drill bit and the bone. The temperature monitoring system also includes a laser configured to emit a light at a location at which the IR sensor is directed. The temperature monitoring system further includes a light emitting diode (LED) configured to indicate the temperature.

In some aspects, the temperature monitoring system is an attachment configured to couple to the drill. The attachment may include a rigid body coupled to a casing. The casing is configured to house the IR sensor, the laser, and the LED. Additionally, or alternatively the system further includes a display device coupled to the attachment. The display device is configured to display the temperature. In some such aspects, the display device further includes a speaker configured to emit an audio output based on the temperature satisfying a threshold. Alternatively, the temperature monitoring system may be integrated into a body of the drill.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding, reference is now made to the following descriptions taken in conjunction with the accompanying drawings, in which:

FIGS. 5A-5C are diagrams of examples of casings in accordance with aspects of the present disclosure;

DETAILED DESCRIPTION

While the following is discussed in terms of a drill, inventive aspects described herein may be applied to other types of tools, e.g., driver tools, that cause heat when utilized in surgery where measurement and control of the heat may be beneficial.

Figure 1:
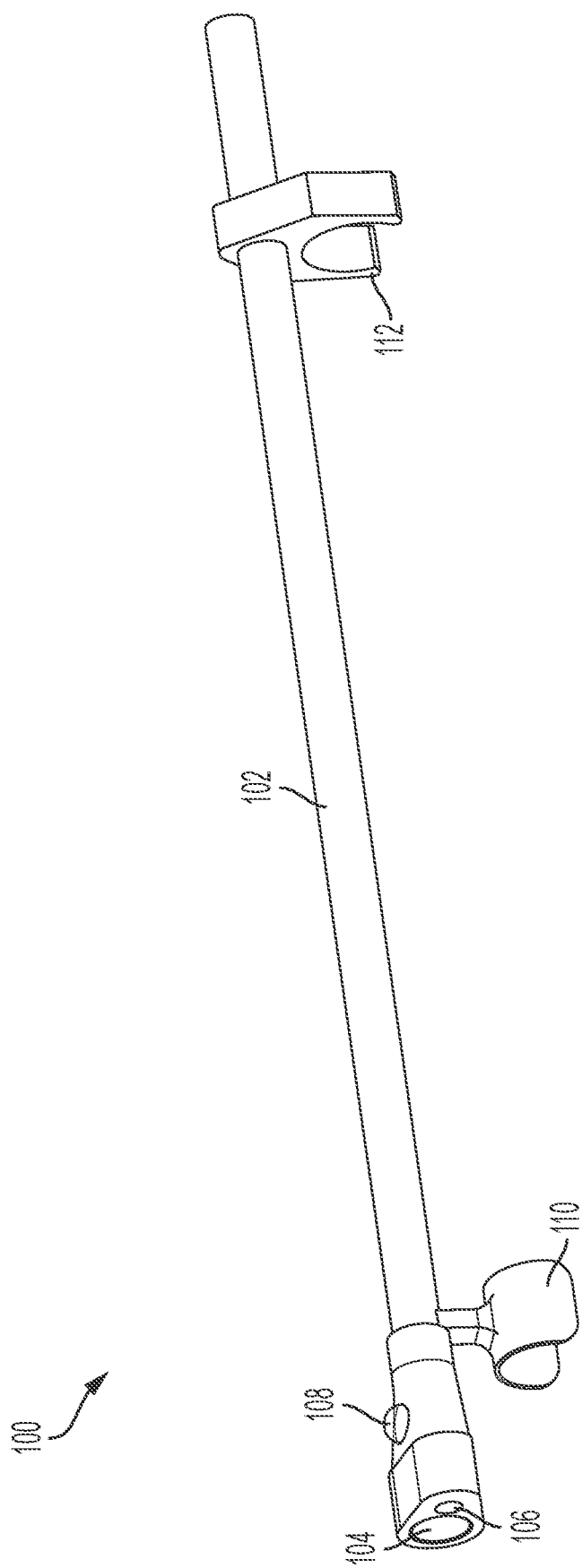
FIG. 1 is a diagram of an example of an attachment with a temperature sensor in accordance with aspects of the present disclosure.

FIG. 1 illustrates an example of an attachment with a temperature sensor for bone temperature measurement. FIG. 1 includes attachment 100. Attachment 100 is referred to as an attachment because, in some implementations, attachment 100 is configured to be coupled to (e.g., attached to) a drill. Attachment 100 includes a rigid body 102, an infrared (IR) sensor 104, a laser 106, and a light emitting diode (LED) 108. Although described as being included in attachment 100, in some implementations, one or more of laser 106 or LED 108 may be optional.

Additionally, rigid body 102 is illustrated as an elongated body that may extend along a tool. It is not necessary that the entire body be rigid. Rather, the body is mountable on a tool (for aspects that are external) in a manner that allows IR sensor 104 and laser 106 to maintain proper orientation to measure and provide feedback for temperature readings. Therefore, any rigidity should provide for such functionality and may comprise a portion or all of body 102.

Rigid body 102 may have a substantially cylindrical shape and may have approximately the same length as a drill to which attachment 100 is designed to be attached. It is appreciated that this length of rigid body 102 may assist in the proper orientation of body 102 along the length of a drill. It is also noted that the length may be shorter. Additionally, having at least two points of contact on the drill may assist in orienting rigid body 102. On one end (e.g., a front end), a casing may be coupled to or be part of rigid body 102. The casing may be configured to house IR sensor 104, laser 106, and LED 108, as further described with reference to FIG. 5. In some implementations, rigid body 102 is hollow and one or more wires (e.g., cords) are run through rigid body to connect IR sensor 104, laser 106, and LED 108 to a processor and a power source (e.g., that are external to attachment 100), as further described with reference to FIG. 3. In some other implementations, IR sensor 104, laser 106, and LED 108 may be wirelessly connected to a processor. In some other implementations, a processor (such as a microprocessor, an application-specific integrated circuit (ASIC), a field-programmable gate array (FPGA), etc.) may be housed within rigid body 102.

IR sensor 104 is configured to measure temperature data indicating a temperature at an interface between a drill bit and a bone of a patient. For example, IR sensor 104 may be an IR thermometer configured to measure a temperature within a field of view (FOV). IR sensor 104 may be fixed within the casing such that the FOV of IR sensor 104 encompasses the end of the drill bit (e.g., the interface where the drill bit meets the bone). As one non-limiting example, IR sensor 104 may include a Melexis™ Infrared Thermometer, which has an operating temperature of 40-85° C., a precision of 0.5° C. within a range of 0-50° C., and a 12° FOV. Although described as an IR sensor, in other implementations, IR sensor 104 may instead by any other type of temperature sensor that is able to measure a temperature at the interface between the drill bit and the bone.

Laser 106 is configured to emit a light at a location where IR sensor 104 is directed. For example, laser 106 may be fixed such that it directs a red light at a center of the FOV of IR sensor 104. Laser 106 may be used when attaching attachment 100 to the drill to ensure that IR sensor 104 is properly aligned with the end of the drill bit. Laser 106 may be turned on or off, so that laser 106 does not emit light during the drilling process.

Embodiments may include LED 108. LED 108 is configured to indicate the temperature measured by IR sensor 104. In some implementations, LED 108 is configured to emit one of a plurality of colored lights based on the temperature indicated by the temperature data. The different colored lights may indicate different temperatures measured by IR sensor 104. For example, LED 108 may be configured to emit a first colored light based on the temperature being within a first temperature range, emit a second colored light based on the temperature being within a second temperature range, and emit a third colored light based on the temperature being within a third temperature range. To illustrate, LED 108 may be configured to emit green light when the temperature is within a first range (e.g., a "safe" range, such as 0-45° C.), LED 108 may be configured to emit a yellow light when the temperature is within a second range (e.g., a "border" range, such as 45-46.5° C.), and LED 108 may be configured to emit a red light when the temperature is within a third range (e.g., a "dangerous" range, such as greater than 46.5° C.). Although three colors for three ranges are described, in other implementations, LED 108 may be configured to emit more than three or less than three colors of light corresponding to different temperature ranges. The example ranges set forth above may also be modified based on preferred uses. For example, it may be preferred to have a broader border range from 40-46.5 degrees, or even to keep the border range top temperature lower than the dangerous range to prevent any crossover (e.g. have the dangerous range begin at 45 degrees).

Additionally, LED 108 may be configured to blink at different stages of temperature readings. Such blinking could be implemented at a single or multiple frequencies. For example, at one temperature range LED 108 may blink slowly, while at another, the blinking may become more rapid. Such blinking may provide an indication of when a first range transitions (or is close to transitioning to a second range. These aspects may also be combined with the color indicators described above. For example, when temperature is in the border range and a yellow light is present. As the temperature raises to approach the dangerous range, the light may start blinking. In more specific embodiments, blinking may begin at a slow period and increase to a faster frequency when close to the dangerous range. It is appreciated that any combination of colors, or blinking patterns may be used based on design preferences.

Attachment 100 also includes one or more attachment clips configured to couple attachment 100 to a drill. For example, attachment 100 may include first attachment clip 110, second attachment clip 112, or both. Attachment clips 110-112 may be configured to clip attachment 100 to a drill. Attachment clips 110-112 may be formed integrally with rigid body 102 or may be coupled to or wrapped around rigid body 102. As an example, rigid body 102 may be formed from plastic, and first attachment clip 110 may be molded from the same plastic and may be attached to (or part of) rigid body 102. As another example, second attachment clip 112 may be wrapped around rigid body 102 and configured to clip to the drill.

In some implementations, IR sensor 104 is coupled (e.g., via wire(s) or wirelessly) to a processor that may control a drill based on the temperature measured by IR sensor 104. For example, IR sensor 104 may provide temperature data to the processor, and the processor may be configured to control power that is provided to the drill. If the temperature satisfies a threshold, the power may be reduced to slow the drill (or reduced to zero to stop the drill) by the processor. Thus, a surgeon (e.g., a user) may rely on an automatic stopping of the drill when the temperature becomes too high.

Thus, FIG. 1 illustrates attachment 100 that includes IR sensor 104 that is configured to measure a temperature at the interface between a drill bit and a bone of a patient. Attachment 100 is configured to provide feedback information to a surgeon (e.g., a user). For example, LED 108 is configured to indicate the temperature (e.g., via outputting different colored lights) to the surgeon, so that the surgeon is able to reduce drill speed or pause drilling when the temperature becomes too high. This may avoid heating the bone to a temperature that causes bone cell death or nerve damage, which can avoid injury to the patient and decrease recovery time after surgery. Additionally, or alternatively, attachment 100 may be coupled to a processor that may reduce power to a drill (or power down the drill) when the temperature satisfies a threshold, thereby automatically stopping the drill when there is a risk of harm to the patient.

Figure 2:
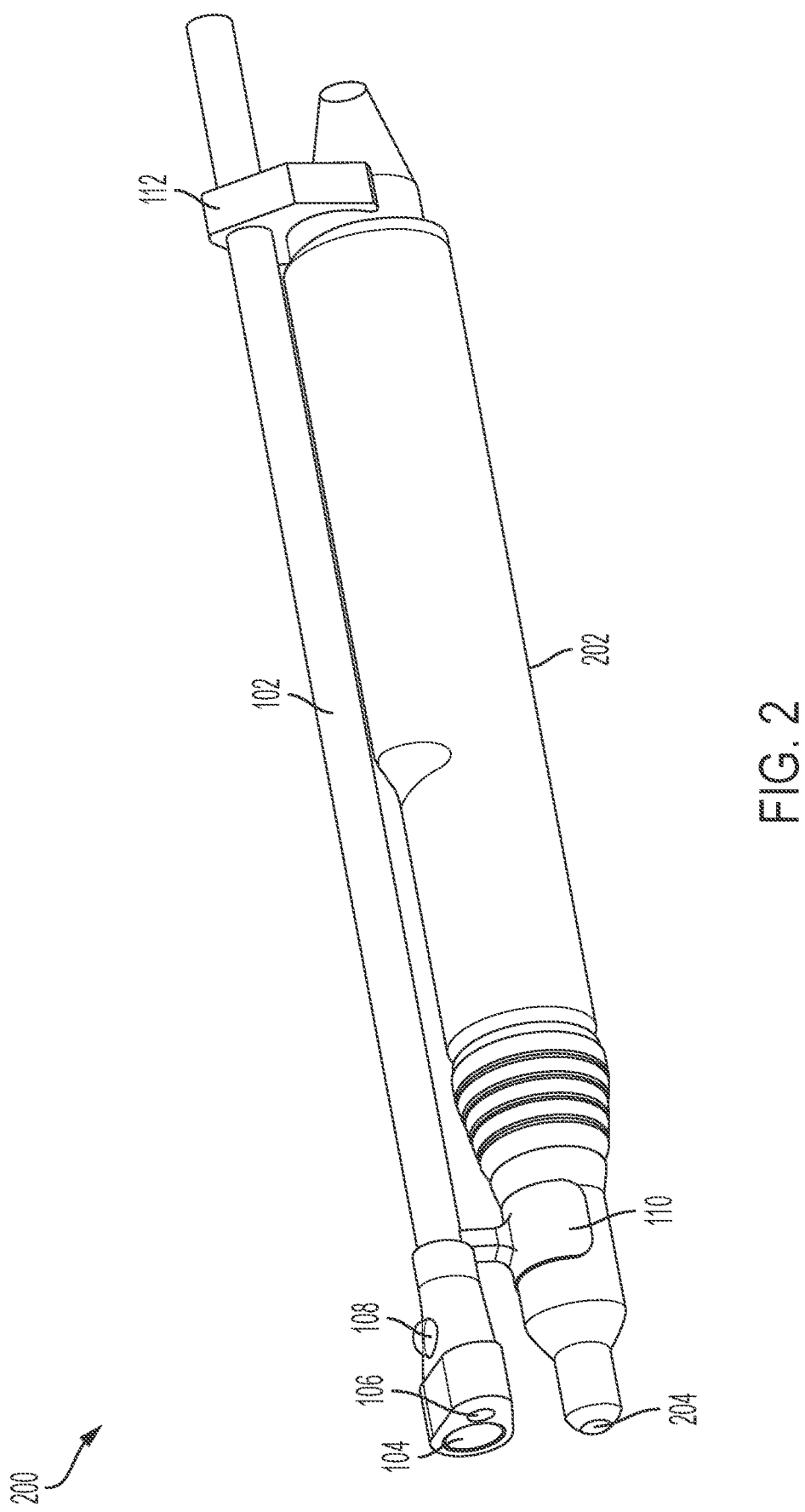
FIG. 2 is a diagram of the attachment of FIG. 1 coupled to a drill in accordance with aspects of the present disclosure.

FIG. 2 illustrates attachment 100 of FIG. 1 coupled to a drill. For example, attachment 100 is coupled to drill 202. Drill 202 may be any type of drill capable of drilling through human bone, such as a drill with a burr drill bit or a straight drill bit, as non-limiting examples.

Attachment 100 may be coupled to drill 202 using first attachment clip 110 and second attachment clip 112. In some implementations, attachment clips 110-112 are configured to snap into place around drill 202, as illustrated in FIG. 2. In other implementations, attachment 100 may be coupled to drill 202 using other components, such as screws, adhesives, or magnets, as non-limiting examples. Further, various drills may be configured to receive specific shapes/sizes of clips 110/112 to ensure a secure attachment.

The front end of attachment 100 (e.g., the end including IR sensor 104 and laser 106) is displaced adjacent to the front end of drill 202. The front end of drill 202 includes opening 204 configured to receive a drill bit (not illustrated for convenience). IR sensor 104 and laser 106 may be fixed within the casing of rigid body 102 such that IR sensor 104 and laser 106 are directed to the end of the drill bit (e.g., such that the end of the drill bit is within the FOV of IR sensor 104).

As can be seen in FIG. 2, attachment 100 is approximately the same length as drill 202 and configured to rest on top of drill 202. Attachment 100 is sufficiently small such that a surgeon can hold the combination of drill 202 and attachment 100 within his or her hand without discomfort and without restricting the surgeon's ability to operate drill 202. Additionally, as explained with reference to FIG. 1, the surgeon is able to know the temperature at the bone by looking at LED 108, which can prevent injury to the patient.

Although described as attachment 100 (e.g., an external component that is coupled to drill 202), in other implementations, components of attachment 100 may be integrated within drill 202. For example, IR sensor 104, laser 106, and LED 108 may be integrated within drill 202. For example, a drill casing may have openings for IR sensor 104 and laser 106, as well as for LED 108, and the components 104-108 may operate as described above as part of drill 202. Thus, the present disclosure contemplates not only attachments to drills, but drills that include temperature sensors.

Figure 3:
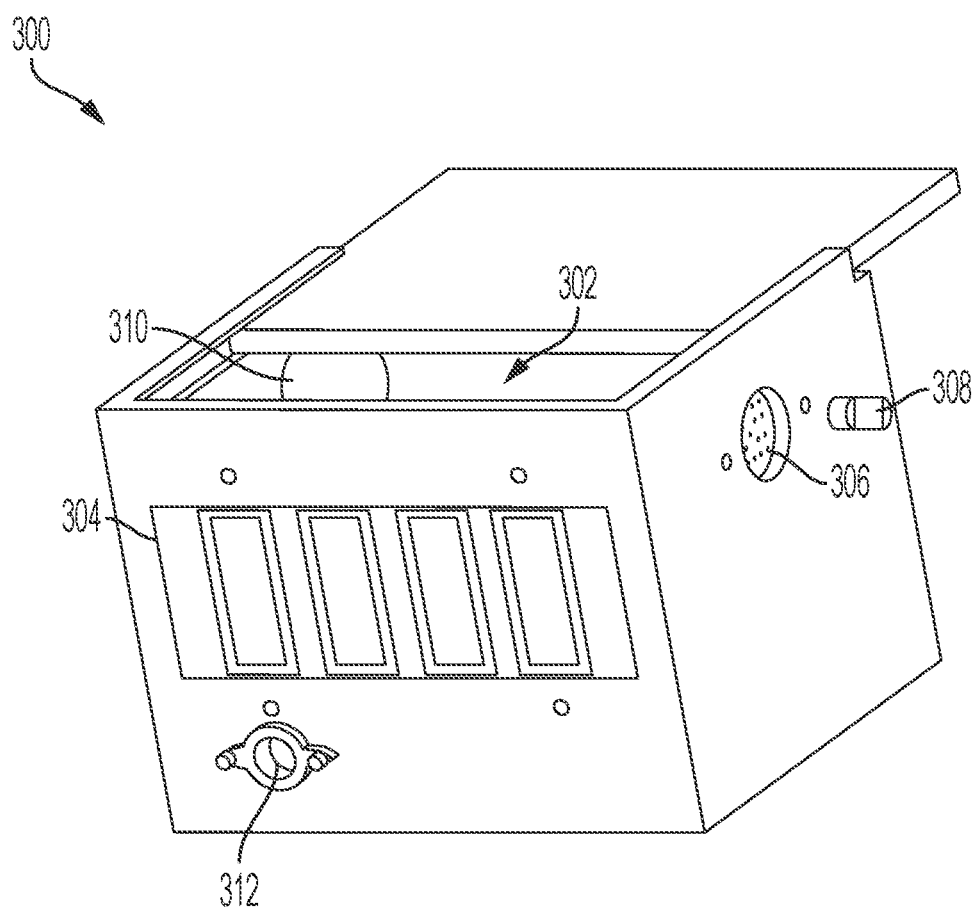
FIG. 3 is a is a diagram of an example of a display device in accordance with aspects of the present disclosure.

FIG. 3 illustrates display component 300. Display component 300 may be external to attachment 100 and coupled to attachment 100 via one or more cords (e.g., wires). Alternatively, display component 300 may be coupled to components of attachment 100 wirelessly. Display component may be configured to display the temperature measured by IR sensor 104 and to emit (e.g., output) audio outputs based on the temperature, as well as house the processor that performs the operations described herein.

Display component 300 includes processor 302, display device 304, speaker 306, volume knob 308, switch 310, and, in some implementations, cord input 312. Processor 302 may execute instructions stored at a memory to perform the operations described herein. Processor 302 is coupled to IR sensor 104, laser 106, LED 108, display device 304, speaker 306, volume knob 308, and switch 310. As illustrated in FIG. 3, processor 302 may be integrated in display component 300. In some implementations, processor 302 is further coupled to a drill control system such that processor 302 may control power provided to the drill based on the temperature measured by IR sensor 104, as described with reference to FIG. 1.

Display device 304 is configured to display the temperature indicated by the temperature data (e.g., generated by IR sensor 104). For example, display device 304 may include a liquid crystal display (LCD) or other display component that displays numbers corresponding to the temperature data. To illustrate, processor 302 may provide the temperature data received from IR sensor 104 (or a processed version thereof) to display device 304 and the display device 304 may display the temperature indicated by the temperature data. Displaying the temperature may enable a surgeon to know, with more detail than the color of LED 108, the temperature at the interface between the drill bit and the bone. In some implementations, display device 304 (e.g., display component 300) is a separate device from IR sensor 104, and display device 304 (e.g., display component 300) is configured to be coupled to IR sensor 104 by a cord.

Speaker 306 is configured to emit an audio output based on the temperature (indicated by the temperature data) satisfying a threshold. For example, if the temperature is within the third temperature range (e.g., the dangerous range, such as above 46.5° C.), speaker 306 may emit an audible sound, such as a beep, an alarm, or some other sound. Additionally, or alternatively, speaker 306 may emit the audio output if the temperature satisfies the threshold for a threshold amount of time. For example, speaker 306 may be configured to emit the audio output if the temperature is greater than 46.5° C. for 20 seconds or more. In other implementations, speaker 306 may be configured to emit an audio output at other times.

In some implementations, display component 300 includes volume knob 308. Volume knob 308 may be configured to adjust the volume of the audio output that is emitted by speaker 306. For example, turning volume knob 308 in one direction may reduce the volume of the audio output, while turning volume knob 308 in an opposite direction may increase the volume of the audio output. In other implementations, volume knob 308 may be replaced with other components, such as buttons, levers, etc., configured to adjust the volume of the audio output.

Switch 310 is configured to switch on or off the components described herein (e.g., display component 300, IR sensor 104, laser 106, and LED 108). For example, when configured in a first position, the components may be turned off, and when configured in a second position, the components may be turned on. Switch 310 may be configured to turn on or off the components by providing a signal to processor 302, which powers up or powers down the components.

Cord input 312 is configured to receive a cord from attachment 100. The cord may electrically couple IR sensor 104, laser 106, and LED 108 to display component 300. Coupling IR sensor 104 to display component 300 may enable processor 302 to receive the temperature data from IR sensor 104. Additionally, coupling LED 108 to display component 300 (e.g., to processor 302) may enable processor 302 to control the light output by LED 108 (based on the temperature data). Additionally, or alternatively, display component 300 may be configured to provide power to IR sensor 104, laser 106, and LED 108. In some other implementations, cord input 312 is not included in display component 300, and IR sensor 104, laser 106, and LED 108 are wirelessly coupled to processor 302. Additionally, any of display device 304, speaker 306, volume knob 308, and switch 310 may be wirelessly coupled to processor 302.

Although display component 300 is illustrated in FIG. 3 as a separate component, in other implementations, one or more components of display component 300 may be integrated into a drill control device. For example, the drill control device may include display device 304 and may be configured to output the temperature measured by IR sensor 104. Additionally, the drill control device may include speaker 306 and may be configured to emit an audio output based on the temperature. In some implementations, processor 302, volume knob 308, switch 310, and/or cord input 312 may also be integrated into the drill control device.

Figure 4:
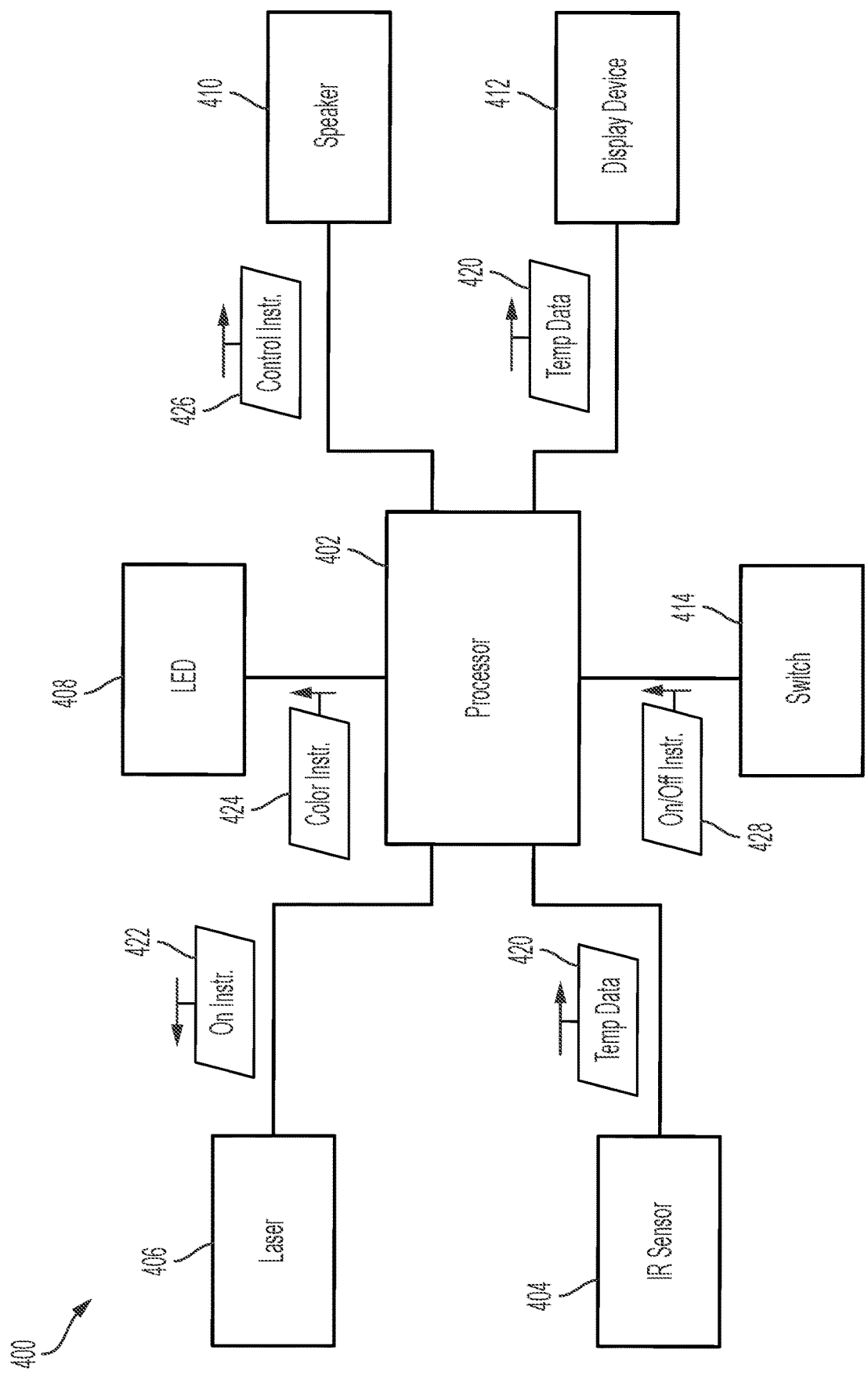
FIG. 4 is a block diagram of an example of a system for measuring the temperature of bone in accordance with aspects of the present disclosure.

FIG. 4 illustrates a system 400 for measuring bone temperature. System 400 includes processor 402, IR sensor 404, laser 406, LED 408, speaker 410, display device 412, and switch 414. In some implementations, processor 402 includes or corresponds to processor 302, IR sensor 404 includes or corresponds to IR sensor 104, laser 406 includes or corresponds to laser 106, LED 408 includes or corresponds to LED 108, speaker 410 includes or corresponds to 306, display device 412 includes or corresponds to display device 304, and switch 414 includes or corresponds to switch 310. It is appreciated that in various aspects, one or more components described with respect to FIG. 4 are optional. For example, speaker 410, LED 408 and display device 412, all provide indications regarding temperature. One or more of these may be left out in some embodiments.

Processor 402 is coupled to IR sensor 404, laser 406, LED 408, speaker 410, display device 412, and switch 414. In some implementations, processor 402 is coupled to one or more of IR sensor 404, laser 406, LED 408, speaker 410, display device 412, and switch 414 via one or more wires. In some other implementations, processor 402 is wirelessly coupled to one or more of IR sensor 404, laser 406, LED 408, speaker 410, display device 412, and switch 414. Processor 402 may be configured to perform the operations described herein.

IR sensor 404 may be configured to measure the temperature at the interface of a drill bit and bone, as described with reference to FIG. 1. IR sensor 404 may be configured to generate temperature data 420 and to provide (e.g., transmit) temperature data 420 to processor 402.

Laser 406 may be configured to emit laser light at a location that indicates a FOV of IR sensor 404. Laser 406 may be configured to be turned on based on an on instruction 422 from processor 402. Similarly, laser 406 may be configured to be turned off by an off instruction received from processor 402.

LED 408 may be configured to emit light or one or more colored light based on instructions from processor 402. For example, LED 408 may be configured to emit a selected color of light indicated by color instruction 424 received from processor 402. LED 408 may also implement the functions discussed above with respect to blinking at various temperature stages and/or a combination of providing blinking and color indications.

Speaker 410 may be configured to emit an audio output. For example, speaker 410 may emit an audio output based on receipt of control instruction 426 from processor 402. Processor 402 may provide control instruction 426 to speaker 410 when the temperature satisfies a threshold, or satisfies the threshold for a threshold amount of time.

Display device 412 may be configured to display the temperature measured by IR sensor 404. For example, display device 412 may receive temperature data 420 from processor 402 and may display the temperature indicated by temperature data 420. In some implementations, processor 402 processes temperature data 420 before providing temperature data 420 to display device 412.

Switch 414 may be configured to initiate a power up or power down of system 400. For example, switch 414 may be configured to provide on/off instruction 428 to processor 402, and processor 402 may power up (or power down) system 400 based on on/off instruction 428.

During operation, a surgeon may operate switch 414 to power on system 400. Switch 414 may transmit on/off instruction 428 to processor 402, and processor 402 may power on the remaining components of system 400. After powering on, processor 402 may provide instruction 422 to laser 406 to power on laser 406. Laser 406 may be powered on long enough to enable a surgeon (e.g., a user) to confirm that IR sensor 404 is properly aligned (e.g., that the FOV of IR sensor 404 includes the tip of the drill bit). After the alignment, processor 402 may provide an off instruction to laser 406 to power down laser 406. In some implementations, the off instruction may be provided after a particular amount of time determined at processor 402. Alternatively, the off instruction may be provided after a user input, such as selection of an off button by the surgeon.

The surgeon may begin using the drill to which system 400 is coupled to (or partially integrated within). IR sensor 404 may begin measuring the temperature at the tip of the drill bit (e.g., in the FOV of IR sensor 404). IR sensor 404 may provide temperature data 420 to processor 402. Temperature data 420 indicates the temperature measured by IR sensor 404.

Based on temperature data 420, processor 402 may provide color instruction 424 to LED 408. For example, based on the measured temperature, processor may select a particular color of light for LED 408 to emit. Color instruction 424 may change as the temperature changes, causing the color of light emitted by LED 408 to change (e.g., from green to yellow as the temperature increases, as one example). Additionally, processor 402 may compare the temperature indicated by temperature data 420 to a threshold, and if the threshold is satisfied (or is satisfied for a threshold amount of time), processor 402 may provide control instruction 426 to speaker 410 to cause speaker 410 to emit an audio output. Additionally, or alternatively, processor 402 may provide temperature data 420 to display device 412 to enable display device 412 to visually output the measured temperature. Additionally, in some implementations, processor 402 may be coupled to a drill control device and may control power provided to the drill based on the measured temperature. For example, if the temperature satisfies a threshold, processor 402 may reduce power to (or power down) the drill to prevent damage to the bone of the patient. Thus, a drill may be automatically stopped when a temperature satisfies a threshold to prevent death of bone cells.

Thus, FIG. 4 illustrates a system (e.g., system 400) that provides valuable information to a surgeon (e.g., a user). For example, an indication of the temperature range at an interface between the drill bit and the bone may be indicated by LED 408. Additionally, a more precise measurement of the temperature may be displayed by display device 412. Additionally, if the temperature satisfies a threshold (or if the threshold is satisfied for a threshold amount of time), speaker 410 may emit an audio output. Thus, a surgeon may be able to perform a bone drilling procedure without allowing the temperature to reach a point that may cause damage to a patient.

FIGS. 5A-5C illustrate casings that may be coupled to (or integrally formed with) rigid body 102 as part of attachment 100. FIG. 5A illustrates a first part 500 of a casing. FIG. 5B illustrates a second part 510 of a casing. FIG. 5C illustrates casing 520 formed by combining first part 500 and second part 510.

As illustrated in FIG. 5A, first part 500 includes a first opening 502 and a second opening 504. First opening 502 is configured to receive an IR sensor, such as IR sensor 104, and second opening 504 is configured to receive a laser, such as laser 106. In some implementations, sidewalls of first opening 502 and sidewalls of second opening 504 are angled such that IR sensor 104 and laser 106 are directed to the tip of a drill bit having a particular length. For example, sidewalls of first opening 502 and sidewalls of second opening 504 may be angled such that IR sensor 104 and laser 106 are directed to the tip of a drill bit having a length of 0.8 inches (in). In such implementations, first part 500 corresponds to a particular drill bit length. If a different drill bit length is used, a different first part 500 (having different angles to the sidewalls of openings 502-504) may be used. In some other implementations, first part 500 may be part of rigid body 102, and an entirely different attachment 100 may be used for different length drill bits. Alternatively, the angles of the sidewalls of openings 502-504 may be adjustable, such that first part 500 (e.g., a single attachment 100) may be used for multiple drill bits having different lengths.

As illustrated in FIG. 5B, second part 510 includes a third opening 512. Third opening 512 may be configured to receive an LED, such as LED 108. For example, LED 108 may be positioned within third opening 512 such that the portion of LED 108 that lights up is visible.

As illustrated in FIG. 5C, first part 500 and second part 510 may be combined to form casing 520. For example, first part 500 and second part 510 may be brazed together. Casing 520 may house IR sensor 104, laser 106, and LED 108. Additionally, an end of casing 520 may be coupled to rigid body 102. Alternatively, second part 510 of casing 520 may be integrally formed with rigid body 102 (while first part 500 is replaceable in some implementations to allow different size drill bits to be used).

Figure 6:
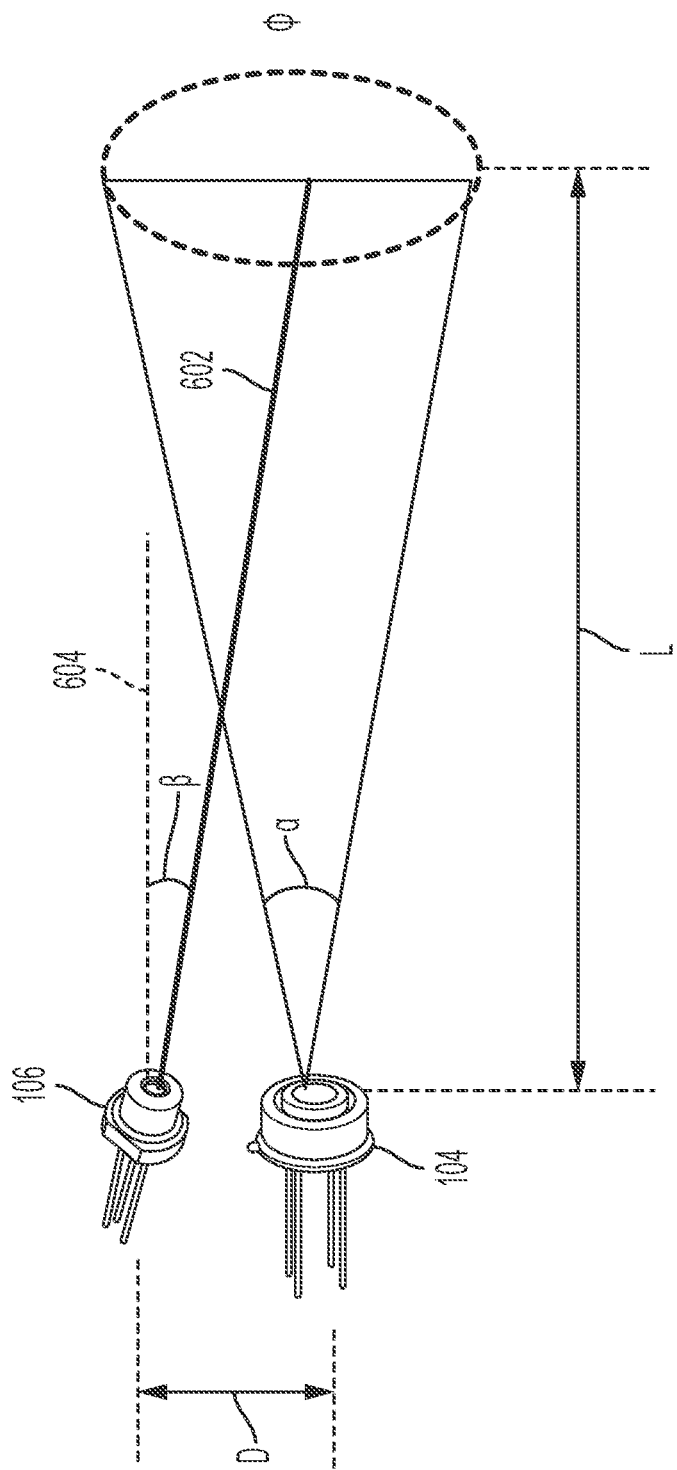
FIG. 6 is a diagram of a temperature sensor and a laser in accordance with aspects of the present disclosure.

FIG. 6 illustrates a temperature sensor and a laser, such as IR sensor 104 and laser 106. FIG. 6 illustrates measurements and angles associated with a particular example of a configuration of IR sensor 104 and laser 106. For example, the configuration may be based on a drill bit having a length L. IR sensor 104 has a FOV $\varphi$ based on angle $\alpha$. Laser 106 may be displaced a distance D from IR sensor 104, and laser 106 may be fixed at an angle β from a horizontal axis 604 in order to emit a laser beam 602 that indicates approximately the center of the FOV of IR sensor 104. In a particular implementation, L is 0.8 inches, D is 0.3 inches, α is 12°, β is 19°, and φ is 0.17 inches. In other implementations, L, D, α, β, and φ have different values. As illustrated in FIG. 6, in some implementations, the alignment between IR sensor 104 and laser 106 is fixed. In some other implementations, laser 106 may be displaced at a different position (e.g., less than distance D) and may be coaxial with IR sensor 104.

Figure 7:
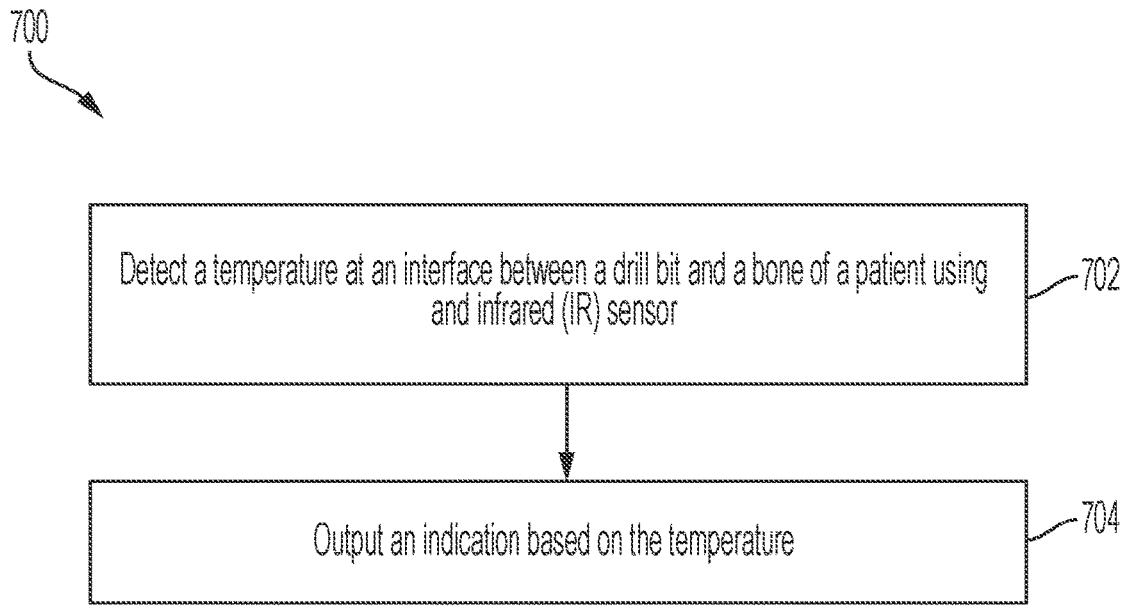
FIG. 7 is a flow chart of an example of a method of bone temperature measurement in accordance with aspects of the present disclosure.

FIG. 7 illustrates a method 700 of bone temperature measurement. Method 700 may be performed by processor 302 and/or by system 400. For example, processor 402 and one or more components of system 400 may perform method 700.

Method 700 includes detecting a temperature at an interface between a drill bit and a bone of a patient using an infrared (IR) sensor, at 702. For example, IR sensor 104 or IR sensor 404 may measure a temperature at an interface between a drill bit and a bone of a patient, and provide temperature data indicating the temperature to processor 302 or processor 402, respectively.

Method 700 further includes outputting an indication based on the temperature, at 704. In some implementations, the indication is a visual indication, and the visual indication is output by a light emitting diode (LED) For example, LED 108 or LED 408 may output a particular color of light based on the temperature being within a particular temperature range. To illustrate, LED 108 or LED 408 may output green light when the temperature is within a safe range, LED 108 or LED 408 may output yellow light when the temperature is within a border range, and LED 108 or LED 408 may output red light when the temperature is within a dangerous range. Additionally or alternatively, the indication is an audio indication, and the audio indication is output by a speaker. For example, speaker 306 or speaker 410 may emit an audible output when the temperature satisfies a threshold, or when the temperature satisfies the threshold for a threshold amount of time.

In some implementations, method 700 further includes visually displaying the temperature at a display device. For example, display device 304 or display device 412 may display the temperature. Additionally, or alternatively, method 700 may further include adjusting a power level provided to a drill based on the temperature. For example, a power level provided to a drill, such as drill 202, may be reduced (or reduced to zero) if the temperature satisfies a threshold.

Thus, method 700 enables the provision of feedback information to a surgeon (e.g., a user) of a drill during a bone drilling process. For example, a color of an LED (or an audio output) may indicate to the surgeon a temperature at the bone of a patient. Providing this information to the surgeon may prevent the surgeon from causing the bone to reach a temperature that may injure the patient. Additionally, or alternatively, the drill may be powered down automatically to prevent injury to the patient.

One or more methods described herein may be implemented as a computer-readable storage device storing instructions that, when executed by a processor, cause the processor to perform the operations corresponding to the method. Additionally, method 700 may further include physical actions such as one or more of attaching the temperature sensor mechanism to the drill itself, powering on the sensor mechanism along with the drill and removing the sensor mechanism when finished with the drilling task.

Figure 8:
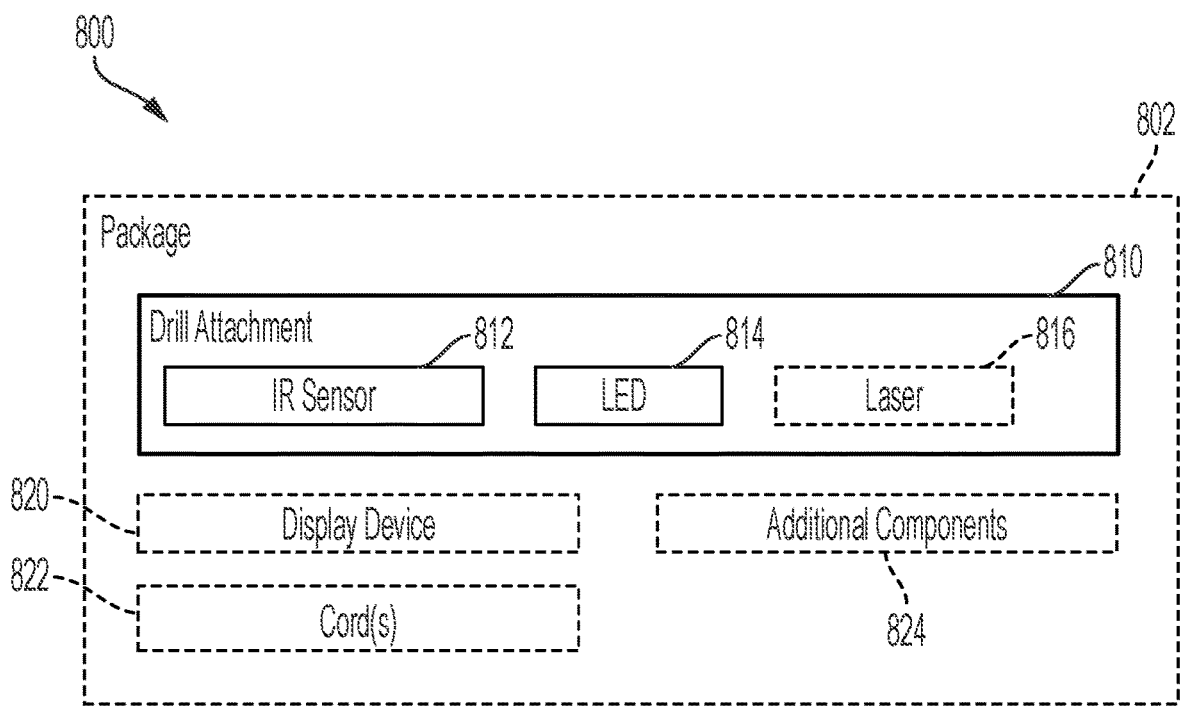
FIG. 8 is a block diagram of an example of a kit for a drill attachment in accordance with aspects of the present disclosure.

Referring to FIG. 8, a kit 800 for a drill attachment is illustrated. Kit 800 includes drill attachment 810. Drill attachment 810 may be configured to be attached to a drill, such as via one or more attachment connectors. Drill attachment 810 may include or correspond to attachment 100 of FIGS. 1-2.

Drill attachment 810 includes an IR sensor 812 and an LED 814. Drill attachment 810 may also include a laser 816 in some implementations. IR sensor 812 may be configured to measure a temperature at an interface of a drill bit of a drill and a bone of a patient. LED 814 may be configured to indicate the temperature, such as by emitting different colored light when the temperature is within different temperature ranges. Laser 816 may be configure to emit a laser beam indicating the FOV of IR sensor 812. IR sensor 812 may include or correspond to IR sensor 104 or IR sensor 404, LED 814 may include or correspond to LED 108 or LED 408, and laser 816 may include or correspond to laser 106 or laser 406.

In some implementations, kit 800 may further include a display device 820, one or more cords 822, additional components 824, or a combination thereof. Display device 820 may be configured to be coupled to drill attachment 810 via one or more cords 822 to display the temperature measured by IR sensor 812. Additional components 824 may include attachment connectors, screws, adhesive, cleaning supplies, batteries, or other components, as non-limiting examples.

In some implementations, kit 800 may include a package 802. For example, package 802 may include a box, a bag, a container, or the like. Package 802 may include drill attachment 810. In some implementations, package 802 may further include display device 820, one or more cords 822, additional components 824, or any combination thereof. Additionally, or alternatively, package 802 may include a packaging medium (e.g., a packaging material), such as foam, paper, or the like. Thus, FIG. 8 describes kit 800 for bone temperature measurement.

It should be understood that the present systems, kits, apparatuses, methods, and computer-readable storage devices are not intended to be limited to the particular forms disclosed. Rather, they are to cover all combination, modifications, equivalents, and alternatives falling within the scope of the claims.

The functional blocks and modules described herein may comprise processors, electronics devices, hardware devices, electronics components, logical circuits, memories, software codes, firmware codes, etc., or any combination thereof.

Those of skill would further appreciate that the various illustrative logical blocks, modules, circuits, and algorithm steps described in connection with the disclosure herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure. Skilled artisans will also readily recognize that the order or combination of components, methods, or interactions that are described herein are merely examples and that the components, methods, or interactions of the various aspects of the present disclosure may be combined or performed in ways other than those illustrated and described herein.

The various illustrative logical blocks, modules, and circuits described in connection with the disclosure herein may be implemented or performed with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the disclosure herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary designs, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. Computer-readable storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, a connection may be properly termed a computer-readable medium. For example, if the software is transmitted from a website, server, or other remote source using a coaxial cable, fiber optic cable, twisted pair, or digital subscriber line (DSL), then the coaxial cable, fiber optic cable, twisted pair, or DSL, are included in the definition of medium. Disk and disc, as used herein, includes compact disc (CD), laser disc, optical disc, digital versatile disc (DVD), hard disk, solid state disk, and Blu-ray disc where disks usually reproduce data magnetically, while discs reproduce data optically with lasers. Combinations of the above should also be included within the scope of computer-readable media.

As used herein, including in the claims, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination. Also, as used herein, including in the claims, "or" as used in a list of items prefaced by "at least one of" indicates a disjunctive list such that, for example, a list of "at least one of A, B, or C" means A or B or C or AB or AC or BC or ABC (i.e., A and B and C) or any of these in any combination thereof.

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein but is to be accorded the widest scope consistent with the principles and novel features disclosed herein.

Although embodiments of the present application and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps. Moreover, the scope of the present application is not intended to be limited to the particular embodiments of the process, machine, manufacture, composition of matter, means, methods and steps described in the specification.

The invention claimed is:

1. An apparatus configured to measure bone temperature during drilling, the apparatus comprising:
a housing configured to mount onto or within a drilling device;
a processor;
an infrared (IR) sensor mounted within the housing and communicatively coupled to the processor, the IR sensor configured to measure temperature data during a drilling action and indicate a temperature at an interface between a drill bit and a bone of a patient; and
a laser configured to emit a light at a location where the IR sensor is directed.

2. The apparatus of claim 1, further comprising a light emitting diode (LED) configured to emit light based on the temperature indicated by the temperature data.

3. The apparatus of claim 2, wherein the LED is configured to:
emit a first colored light based on the temperature being within a first temperature range;
emit a second colored light based on the temperature being within a second temperature range; and emit a third colored light based on the temperature being within a third temperature range.

4. The apparatus of claim 1, further comprising a speaker configured to emit an audio output based on the temperature indicated by the temperature data satisfying a threshold.

5. The apparatus of claim 1, further comprising a display device configured to display the temperature indicated by the temperature data.

6. The apparatus of claim 5, wherein the display device is a separate device from the IR sensor, and wherein the display device is configured to be coupled to the IR sensor by a cord.

7. The apparatus of claim 1, wherein the housing comprises an elongated rigid body coupled to the IR sensor.

8. The apparatus of claim 7, wherein the elongated rigid body comprises an attachment to a drill.

9. The apparatus of claim 8, wherein the elongated rigid body further comprises one or more attachment clips configured to couple the attachment to the drill.

10. The apparatus of claim 1, wherein the IR sensor is integrated within a drill.

11. A method of measuring bone temperature during drilling, the method comprising:
    transmitting a laser light onto a target area of a bone of a patient at an interface between a drill bit and the bone;
    detecting a temperature at the interface between the drill bit and the bone of the patient using an infrared (IR) sensor mounted to a drilling device; and
    outputting an indication based on the temperature.

12. The method of claim 11, wherein the indication is a visual indication, and wherein the visual indication is output by a light emitting diode.

13. The method of claim 11, further comprising visually displaying the temperature at a display device.

14. The method of claim 11, further comprising automatically adjusting a power level provided to a drill by a processing device based on the detected temperature.

15. A system comprising:
    a drill configured to drill into bone of a patient, the drill including a drill bit; and
    a temperature monitoring system controlled by one or more processors, said temperature monitoring system comprising:
        an infrared (IR) sensor configured to measure a temperature at an interface of the drill bit and the bone;
        a laser configured to emit a light at a location at which the IR sensor is directed; and
        a light emitting diode (LED) configured to indicate the temperature.

16. The system of claim 15, wherein the temperature monitoring system is an attachment configured to couple to the drill.

17. The system of claim 16, wherein the attachment comprises a rigid body coupled to a casing, and wherein the casing is configured to house the IR sensor, the laser, and the LED.

18. The system of claim 15, further comprising a display device coupled to the attachment, the display device configured to display the temperature.

19. The system of claim 18, wherein the display device further comprises a speaker configured to emit an audio output based on the temperature satisfying a threshold.

20. The system of claim 15, wherein the temperature monitoring system is integrated into a body of the drill.

21. The system of claim 15, wherein the LED is configured to display a plurality of colors of light to indicate that the temperature is within a range corresponding to a displayed color.

22. The system of claim 21, wherein the LED is configured to blink at one or more frequencies corresponding to one or more ranges of temperature.

* * * * *